(12) United States Patent
Krone et al.

(10) Patent No.: US 10,413,408 B2
(45) Date of Patent: Sep. 17, 2019

(54) DELIVERY CATHETER SYSTEMS, METHODS, AND DEVICES

(71) Applicant: Evalve, Inc., Menlo Park, CA (US)

(72) Inventors: Ryan T. Krone, San Francisco, CA (US); Francisco Valencia, East Palo Alto, CA (US); Manish Gada, Santa Clara, CA (US)

(73) Assignee: Evalve, Inc., Santa Clara, CA (US)

( * ) Notice: Subject to any disclaimer, the term of this patent is extended or adjusted under 35 U.S.C. 154(b) by 658 days.

(21) Appl. No.: 14/820,141

(22) Filed: Aug. 6, 2015

(65) Prior Publication Data

US 2017/0035566 A1 Feb. 9, 2017

(51) Int. Cl.
| | |
|---|---|
| *A61F 2/24* | (2006.01) |
| *A61F 2/95* | (2013.01) |
| *A61M 25/00* | (2006.01) |
| *A61M 25/01* | (2006.01) |

(52) U.S. Cl.
CPC ....... *A61F 2/2427* (2013.01); *A61M 25/0026* (2013.01); *A61M 25/0147* (2013.01); *A61F 2/95* (2013.01); *A61F 2002/9517* (2013.01); *A61M 25/005* (2013.01); *A61M 25/0045* (2013.01); *A61M 2025/004* (2013.01); *A61M 2025/0036* (2013.01)

(58) Field of Classification Search
CPC .......... A61M 25/0026; A61M 25/0045; A61M 25/005; A61M 25/0012; A61M 2025/004; A61M 2025/0036
See application file for complete search history.

(56) References Cited

U.S. PATENT DOCUMENTS

| | | | |
|---|---|---|---|
| 2,097,018 | A | 10/1937 | Chamberlain |
| 2,108,206 | A | 2/1938 | Meeker |
| 3,296,668 | A | 1/1967 | Aiken |
| 3,378,010 | A | 4/1968 | Codling et al. |
| 3,557,780 | A | 1/1971 | Sato |
| 3,675,639 | A | 7/1972 | Cimber |
| 3,874,388 | A | 4/1975 | King et al. |
| 4,007,743 | A | 2/1977 | Blake |
| 4,064,881 | A | 12/1977 | Meredith |
| 4,091,815 | A | 5/1978 | Larsen |

(Continued)

FOREIGN PATENT DOCUMENTS

| | | |
|---|---|---|
| CN | 102258402 | 11/2014 |
| DE | 3504292 | 7/1986 |

(Continued)

OTHER PUBLICATIONS

Modulus of Elasticity-Young Modulus for some common Materials, http://www.bestech.com.au/wp-content/uploads/Modulus-of-Elasticity.pdf, Jan. 16, 2018.*

(Continued)

*Primary Examiner* — Diane D Yabut
*Assistant Examiner* — Majid Jamialahmadi
(74) *Attorney, Agent, or Firm* — Workman Nydegger

(57) ABSTRACT

An intravascular device includes a shaft having a body defining a major lumen and a plurality of minor lumen. The minor lumens are spaced about the major lumen. The major lumen and the plurality of minor lumen extend from a proximal end of the body to a distal end of the body. One or more wires may extend through the major lumen and/or minor lumen.

16 Claims, 7 Drawing Sheets

(56) References Cited

U.S. PATENT DOCUMENTS

| | | | |
|---|---|---|---|
| 4,112,951 | A | 9/1978 | Hulka et al. |
| 4,235,238 | A | 11/1980 | Ogiu et al. |
| 4,297,749 | A | 11/1981 | Davis et al. |
| 4,458,682 | A | 7/1984 | Cerwin |
| 4,425,908 | A | 11/1984 | Simon |
| 4,487,205 | A | 12/1984 | Di Giovanni et al. |
| 4,498,476 | A | 2/1985 | Cerwin et al. |
| 4,510,934 | A | 4/1985 | Batra |
| 4,531,522 | A | 7/1985 | Bedi et al. |
| 4,578,061 | A | 3/1986 | Lemelson |
| 4,641,366 | A | 2/1987 | Yokoyama et al. |
| 4,686,965 | A | 8/1987 | Bonnet et al. |
| 4,777,951 | A | 10/1988 | Cribier et al. |
| 4,809,695 | A | 3/1989 | Gwathmey et al. |
| 4,896,986 | A | 1/1990 | Terayama |
| 4,944,295 | A | 7/1990 | Gwathmey et al. |
| 4,969,890 | A | 11/1990 | Sugita et al. |
| 5,015,249 | A | 5/1991 | Nakao et al. |
| 5,019,096 | A | 5/1991 | Fox, Jr. et al. |
| 5,042,161 | A | 8/1991 | Hodge |
| 5,042,707 | A | 8/1991 | Taheri |
| 5,047,041 | A | 9/1991 | Samuels |
| 5,049,153 | A | 9/1991 | Nakao et al. |
| 5,061,277 | A | 10/1991 | Carpentier et al. |
| 5,069,679 | A | 12/1991 | Taheri |
| 5,108,368 | A | 4/1992 | Hammerslag et al. |
| 5,125,758 | A | 6/1992 | DeWan |
| 5,171,252 | A | 12/1992 | Friedland |
| 5,171,259 | A | 12/1992 | Inoue |
| 5,190,554 | A | 3/1993 | Coddington et al. |
| 5,195,968 | A | 3/1993 | Lundquist et al. |
| 5,209,756 | A | 5/1993 | Seedhom et al. |
| 5,226,429 | A | 7/1993 | Kuzmak |
| 5,226,911 | A | 7/1993 | Chee et al. |
| 5,234,437 | A | 8/1993 | Sepetka |
| 5,236,450 | A | 8/1993 | Scott |
| 5,242,456 | A | 9/1993 | Nash et al. |
| 5,250,071 | A | 10/1993 | Palermo |
| 5,251,611 | A | 10/1993 | Zehel et al. |
| 5,254,130 | A | 10/1993 | Poncet et al. |
| 5,261,916 | A | 11/1993 | Engelson |
| 5,263,939 | A | 11/1993 | Wortrich |
| 5,271,381 | A | 12/1993 | Ailinger et al. |
| 5,275,578 | A | 1/1994 | Adams |
| 5,282,845 | A | 2/1994 | Bush et al. |
| 5,304,131 | A | 4/1994 | Paskar |
| 5,306,283 | A | 4/1994 | Conners |
| 5,306,286 | A | 4/1994 | Stack et al. |
| 5,312,415 | A | 5/1994 | Palermo |
| 5,314,424 | A | 5/1994 | Nicholas |
| 5,318,525 | A | 6/1994 | West et al. |
| 5,320,632 | A | 6/1994 | Heidmueller |
| 5,325,845 | A | 7/1994 | Adair |
| 5,330,442 | A | 7/1994 | Green et al. |
| 5,342,393 | A | 8/1994 | Stack |
| 5,350,397 | A | 9/1994 | Palermo et al. |
| 5,350,399 | A | 9/1994 | Erlebacher et al. |
| 5,359,994 | A | 11/1994 | Kreuter et al. |
| 5,368,564 | A | 11/1994 | Savage |
| 5,368,601 | A | 11/1994 | Sauer et al. |
| 5,383,886 | A | 1/1995 | Kensey et al. |
| 5,391,182 | A | 2/1995 | Chin |
| 5,403,312 | A | 4/1995 | Yates et al. |
| 5,403,326 | A | 4/1995 | Harrison et al. |
| 5,405,402 | A | 4/1995 | Dye et al. |
| 5,417,699 | A | 5/1995 | Klein et al. |
| 5,417,700 | A | 5/1995 | Egan |
| 5,423,857 | A | 6/1995 | Rosenman et al. |
| 5,423,858 | A | 6/1995 | Bolanos et al. |
| 5,423,882 | A | 6/1995 | Jackman et al. |
| 5,431,666 | A | 7/1995 | Sauer et al. |
| 5,437,551 | A | 8/1995 | Chalifoux |
| 5,437,681 | A | 8/1995 | Meade et al. |
| 5,447,966 | A | 9/1995 | Hermes et al. |
| 5,450,860 | A | 9/1995 | O'Connor |
| 5,456,400 | A | 10/1995 | Shichman et al. |
| 5,456,684 | A | 10/1995 | Schmidt et al. |
| 5,462,527 | A | 10/1995 | Stevens-Wright et al. |
| 5,464,394 | A * | 11/1995 | Miller ............... A61M 25/005 604/103.1 |
| 5,472,044 | A | 12/1995 | Hall et al. |
| 5,476,470 | A | 12/1995 | Fitzgibbons, Jr. |
| 5,477,856 | A | 12/1995 | Lundquist |
| 5,478,309 | A | 12/1995 | Sweezer et al. |
| 5,478,353 | A | 12/1995 | Yoon |
| 5,487,746 | A | 1/1996 | Yu et al. |
| 5,489,296 | A | 2/1996 | Love et al. |
| 5,496,332 | A | 3/1996 | Sierra et al. |
| 5,507,725 | A | 4/1996 | Savage et al. |
| 5,507,755 | A | 4/1996 | Gresl et al. |
| 5,507,757 | A | 4/1996 | Sauer et al. |
| 5,520,701 | A | 5/1996 | Lerch |
| 5,522,873 | A | 6/1996 | Jackman et al. |
| 5,527,313 | A | 6/1996 | Scott et al. |
| 5,527,321 | A | 6/1996 | Hinchliffe |
| 5,527,322 | A | 6/1996 | Klein et al. |
| 5,536,251 | A | 7/1996 | Evard et al. |
| 5,540,705 | A | 7/1996 | Meade et al. |
| 5,542,949 | A | 8/1996 | Yoon |
| 5,562,678 | A | 10/1996 | Booker |
| 5,569,274 | A | 10/1996 | Rapacki et al. |
| 5,571,085 | A | 11/1996 | Accisano, III |
| 5,571,137 | A | 11/1996 | Marlow et al. |
| 5,571,215 | A | 11/1996 | Sterman et al. |
| 5,575,802 | A | 11/1996 | McQuilkin et al. |
| 5,582,611 | A | 12/1996 | Tsuruta et al. |
| 5,593,424 | A | 1/1997 | Northrup, III |
| 5,593,435 | A | 1/1997 | Carpentier et al. |
| 5,609,598 | A | 3/1997 | Laufer et al. |
| 5,618,306 | A | 4/1997 | Roth et al. |
| 5,620,452 | A | 4/1997 | Yoon |
| 5,620,461 | A | 4/1997 | Muijs Van De Moer et al. |
| 5,626,588 | A | 5/1997 | Sauer et al. |
| 5,630,832 | A | 5/1997 | Giordano et al. |
| 5,634,932 | A | 6/1997 | Schmidt |
| 5,636,634 | A | 6/1997 | Kordis et al. |
| 5,639,277 | A | 6/1997 | Mariant et al. |
| 5,640,955 | A | 6/1997 | Ockuly et al. |
| 5,649,937 | A | 7/1997 | Bito et al. |
| 5,662,606 | A | 9/1997 | Cimino et al. |
| 5,662,681 | A | 9/1997 | Nash et al. |
| 5,669,917 | A | 9/1997 | Sauer et al. |
| 5,690,671 | A | 11/1997 | McGurk et al. |
| 5,695,504 | A | 12/1997 | Gifford, III et al. |
| 5,695,505 | A | 12/1997 | Yoon |
| 5,702,825 | A | 12/1997 | Keital et al. |
| 5,706,824 | A | 1/1998 | Whittier |
| 5,709,707 | A | 1/1998 | Lock et al. |
| 5,713,910 | A | 2/1998 | Gordon et al. |
| 5,713,911 | A | 2/1998 | Racene et al. |
| 5,715,817 | A | 2/1998 | Stevens-Wright et al. |
| 5,716,367 | A | 2/1998 | Koike et al. |
| 5,718,714 | A | 2/1998 | Livneh |
| 5,719,725 | A | 2/1998 | Nakao |
| 5,722,421 | A | 3/1998 | Francese et al. |
| 5,725,542 | A | 3/1998 | Yoon |
| 5,725,556 | A | 3/1998 | Moser et al. |
| 5,738,649 | A | 4/1998 | Macoviak |
| 5,741,280 | A | 4/1998 | Fleenor |
| 5,741,286 | A | 4/1998 | Recuset |
| 5,749,828 | A | 5/1998 | Solomon et al. |
| 5,759,193 | A | 6/1998 | Burbank et al. |
| 5,769,863 | A | 6/1998 | Garrison |
| 5,772,578 | A | 6/1998 | Heimberger et al. |
| 5,782,845 | A | 7/1998 | Shewchuk |
| 5,797,927 | A | 8/1998 | Yoon |
| 5,810,847 | A | 9/1998 | Laufer et al. |
| 5,810,849 | A | 9/1998 | Kontos |
| 5,810,853 | A | 9/1998 | Yoon |
| 5,810,876 | A | 9/1998 | Kelleher |
| 5,814,029 | A | 9/1998 | Hassett |
| 5,820,592 | A | 10/1998 | Hammerslag |
| 5,820,631 | A | 10/1998 | Nobles |
| 5,823,955 | A | 10/1998 | Kuck et al. |

(56) References Cited

U.S. PATENT DOCUMENTS

| | | |
|---|---|---|
| 5,824,065 A | 10/1998 | Gross |
| 5,827,237 A | 10/1998 | Macoviak et al. |
| 5,833,671 A | 11/1998 | Macoviak et al. |
| 5,836,955 A | 11/1998 | Buelna et al. |
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,860,990 A | 1/1999 | Nobles et al. |
| 5,861,003 A | 1/1999 | Latson et al. |
| 5,868,733 A | 2/1999 | Ockuly et al. |
| 5,871,493 A | 2/1999 | Sjostrom et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,902,290 A * | 5/1999 | Peacock, III ..... A61M 25/0052 604/264 |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,964,717 A | 10/1999 | Gottlieb et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,993,470 A | 11/1999 | Yoon |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,214 A | 10/2000 | Zirps et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,350,281 B1 | 2/2002 | Rhee |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |

(56) References Cited

U.S. PATENT DOCUMENTS

| | | |
|---|---|---|
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 8,216,256 B2 | 7/2012 | Raschdorf, Jr. et al. |
| D668,334 S | 10/2012 | Makowski et al. |
| D740,414 S | 10/2015 | Katsura |
| D809,139 S | 1/2018 | Marsot et al. |
| 2001/0004715 A1 | 6/2001 | Duran et al. |
| 2001/0005787 A1 | 6/2001 | Oz et al. |
| 2001/0007067 A1 | 7/2001 | Kurfess et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0181855 A1 | 9/2003 | Simpson et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138529 A1 | 7/2004 | Wiltshire et al. |
| 2004/0138675 A1 | 7/2004 | Crabtree |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0199052 A1 | 10/2004 | Banik et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243227 A1 | 12/2004 | Starksen et al. |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0006432 A1 | 1/2005 | Racenet et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0009715 A1 | 1/2006 | Khairkhahan et al. |

(56) References Cited

U.S. PATENT DOCUMENTS

| | | |
|---|---|---|
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2006/0287643 A1 | 12/2006 | Perlin |
| 2007/0038293 A1 | 2/2007 | St. Goar et al. |
| 2007/0088277 A1 | 4/2007 | McGinley et al. |
| 2007/0088431 A1 | 4/2007 | Bourang et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0154299 A1 | 6/2008 | Livneh |
| 2008/0167714 A1 | 7/2008 | St. Goer et al. |
| 2008/0183194 A1 | 7/2008 | Goldfarb et al. |
| 2009/0143851 A1 | 6/2009 | Paul, Jr. |
| 2009/0156995 A1 | 6/2009 | Martin et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0168717 A1 | 7/2010 | Grasse et al. |
| 2010/0217184 A1* | 8/2010 | Koblish ............ A61M 25/0141 604/95.01 |
| 2010/0252293 A1 | 10/2010 | Lopano et al. |
| 2011/0077498 A1* | 3/2011 | McDaniel .......... A61B 18/1492 600/374 |
| 2011/0190778 A1* | 8/2011 | Arpasi .............. A61M 25/0026 606/108 |
| 2012/0089136 A1 | 4/2012 | Levin et al. |
| 2012/0253329 A1 | 10/2012 | Zemlok et al. |
| 2012/0330408 A1 | 12/2012 | Hillukka et al. |
| 2013/0053822 A1 | 2/2013 | Fischell et al. |
| 2013/0066342 A1 | 3/2013 | Dell et al. |
| 2013/0304117 A1 | 11/2013 | Sugiyama |
| 2013/0310813 A1 | 11/2013 | Kaercher et al. |
| 2014/0012287 A1 | 1/2014 | Oyola et al. |
| 2014/0025103 A1 | 1/2014 | Hundertmark et al. |
| 2014/0148651 A1 | 5/2014 | Aman et al. |
| 2014/0148673 A1 | 5/2014 | Bogusky |
| 2014/0171923 A1 | 6/2014 | Aranyi |
| 2014/0196923 A1 | 7/2014 | Leupert et al. |
| 2014/0243969 A1* | 8/2014 | Venkatasubramanian ................... A61F 2/2412 623/2.38 |
| 2015/0060516 A1 | 3/2015 | Collings et al. |
| 2015/0182334 A1 | 7/2015 | Bourang et al. |
| 2015/0306806 A1* | 10/2015 | Dando ................ B29C 47/0026 264/515 |
| 2016/0174979 A1 | 6/2016 | Wei |
| 2016/0367787 A1 | 12/2016 | Van Hoven et al. |
| 2016/0374811 A1 | 12/2016 | McNiven et al. |
| 2017/0100250 A1 | 4/2017 | Marsot et al. |

FOREIGN PATENT DOCUMENTS

| | | |
|---|---|---|
| DE | 10116168 | 11/2001 |
| EP | 0179562 | 7/1989 |
| EP | 0558031 | 2/1993 |
| EP | 0684012 | 11/1995 |
| EP | 0727239 | 8/1996 |
| EP | 0782836 | 7/1997 |
| EP | 0990449 | 4/2000 |
| EP | 1230899 | 8/2002 |
| EP | 1674040 | 6/2006 |
| EP | 2465568 | 6/2012 |
| FR | 2768324 | 3/1999 |
| GB | 1598111 | 9/1981 |
| GB | 2151142 | 7/1985 |
| GB | 2222951 | 3/1990 |
| JP | H 09253030 | 9/1997 |
| JP | H 11089937 | 4/1999 |
| JP | 2000283130 | 10/2000 |
| JP | 2015502548 | 1/2015 |
| WO | WO 1981000668 | 3/1981 |
| WO | WO 1991018881 | 12/1991 |
| WO | WO 1992012690 | 8/1992 |
| WO | WO 1994018881 | 9/1994 |
| WO | WO 1994018893 | 9/1994 |
| WO | WO 1995011620 | 5/1995 |
| WO | WO 1995015715 | 6/1995 |
| WO | WO 1996014032 | 5/1996 |
| WO | WO 1996020655 | 7/1996 |
| WO | WO 1996022735 | 8/1996 |
| WO | WO 1996030072 | 10/1996 |
| WO | WO 1997018746 | 5/1997 |
| WO | WO 1997025927 | 7/1997 |
| WO | WO 1997026034 | 7/1997 |
| WO | WO 1997038748 | 10/1997 |
| WO | WO 1997039688 | 10/1997 |
| WO | WO 1997048436 | 12/1997 |
| WO | WO 1998007375 | 2/1998 |
| WO | WO 1998024372 | 6/1998 |
| WO | WO 1998030153 | 7/1998 |
| WO | WO 1998032382 | 7/1998 |
| WO | WO 1999007354 | 2/1999 |
| WO | WO 1999013777 | 3/1999 |
| WO | WO 1999066967 | 12/1999 |
| WO | WO 2000002489 | 1/2000 |
| WO | WO 2000003651 | 1/2000 |
| WO | WO 2000012168 | 3/2000 |
| WO | WO 2000044313 | 8/2000 |
| WO | WO 2000059382 | 10/2000 |
| WO | WO 2001000111 | 1/2001 |
| WO | WO 2001000114 | 1/2001 |
| WO | WO 2001003651 | 1/2001 |
| WO | WO 2001026557 | 4/2001 |
| WO | WO 2001026586 | 4/2001 |
| WO | WO 2001026587 | 4/2001 |
| WO | WO 2001026588 | 4/2001 |
| WO | WO 2001026703 | 4/2001 |
| WO | WO 2001028432 | 4/2001 |
| WO | WO 2001028455 | 4/2001 |
| WO | WO 2001047438 | 7/2001 |
| WO | WO 2001049213 | 7/2001 |
| WO | WO 2001050985 | 7/2001 |
| WO | WO 2001054618 | 8/2001 |
| WO | WO 2001056512 | 8/2001 |
| WO | WO 2001066001 | 9/2001 |
| WO | WO 2001070320 | 9/2001 |
| WO | WO 2001089440 | 11/2001 |
| WO | WO 2001095831 | 12/2001 |
| WO | WO 2001095832 | 12/2001 |
| WO | WO 2001097741 | 12/2001 |
| WO | WO 2002000099 | 1/2002 |
| WO | WO 2002001999 | 1/2002 |
| WO | WO 2002003892 | 1/2002 |
| WO | WO 2002034167 | 5/2002 |
| WO | WO 2002060352 | 8/2002 |
| WO | WO 2002062263 | 8/2002 |
| WO | WO 2002062270 | 8/2002 |
| WO | WO 2002062408 | 8/2002 |
| WO | WO 2003001893 | 1/2003 |

(56) References Cited

FOREIGN PATENT DOCUMENTS

| | | |
|---|---|---|
| WO | WO 2003003930 | 1/2003 |
| WO | WO 2003020179 | 3/2003 |
| WO | WO 2003028558 | 4/2003 |
| WO | WO 2003037171 | 5/2003 |
| WO | WO 2003047467 | 6/2003 |
| WO | WO 2003049619 | 6/2003 |
| WO | WO 2003073910 | 9/2003 |
| WO | WO 2003073913 | 9/2003 |
| WO | WO 2003082129 | 10/2003 |
| WO | WO 2003105667 | 12/2003 |
| WO | WO 2004004607 | 1/2004 |
| WO | WO 2004012583 | 2/2004 |
| WO | WO 2004012789 | 2/2004 |
| WO | WO 2004014282 | 2/2004 |
| WO | WO 2004019811 | 3/2004 |
| WO | WO 2004030570 | 4/2004 |
| WO | WO 2004037317 | 5/2004 |
| WO | WO 2004045370 | 6/2004 |
| WO | WO 2004045378 | 6/2004 |
| WO | WO 2004045463 | 6/2004 |
| WO | WO 2004047679 | 6/2004 |
| WO | WO 2004062725 | 7/2004 |
| WO | WO 2004082523 | 9/2004 |
| WO | WO 2004082538 | 9/2004 |
| WO | WO 2004093730 | 11/2004 |
| WO | WO 2004103162 | 12/2004 |
| WO | WO 2004112585 | 12/2004 |
| WO | WO 2004112651 | 12/2004 |
| WO | WO 2005002424 | 1/2005 |
| WO | WO 2005018507 | 3/2005 |
| WO | WO 2005027797 | 3/2005 |
| WO | WO 2005032421 | 4/2005 |
| WO | WO 2005062931 | 7/2005 |
| WO | WO 2005112792 | 12/2005 |
| WO | WO 2006037073 | 4/2006 |
| WO | WO 2006105008 | 10/2006 |
| WO | WO 2006105009 | 10/2006 |
| WO | WO 2006115875 | 11/2006 |
| WO | WO 2006115876 | 11/2006 |
| WO | WO2007/047488 | 4/2007 |
| WO | WO2008/031103 | 3/2008 |
| WO | WO 2014182797 | 11/2014 |
| WO | WO2015/061052 | 4/2015 |
| WO | WO 2016204954 | 12/2016 |
| WO | WO 2017003606 | 1/2017 |
| WO | WO 2017/023534 | 2/2017 |

OTHER PUBLICATIONS

U.S. Appl. No. 14/216,787, filed Mar. 17, 2014, Basude et al.
U.S. Appl. No. 15/662,084, filed Jul. 27, 2017, Prabhu et al.
U.S. Appl. No. 29/633,930, filed Jan. 17, 2018, Marsot et al.
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The edge to edge technique," The European Association for Cardio-Thoracic Surgery 14th Annual Meeting, Oct. 7-11, 2000, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Arisi et al., "Mitral Valve Repair with Alfieri Technique in Mitral Regurgitation of Diverse Etiology: Early Echocardiographic Results," Circulation Supplement II, 104(17):3240 (2001).
Bailey, "Mitral Regurgitation" in Surgery of the Heart, Chapter 20, pp. 686-737 (1955).

Bernal et al., "The Valve Racket: a new and different concept of atrioventricular valve repair," Eur J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. For Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172-175.
Gatti et al., "The edge to edge technique as a trick to rescue an imperfect mitral valve repair," Eur J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annuals of Thoracic Surgery, 67:1703-1707 (1999).

(56) References Cited

OTHER PUBLICATIONS

Kallner et al., "Transaortic Approach for the Alfieri Stitch," Ann Thorac Surg, 71:378-380 (2001).
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Robicsek et al., #60 The Bicuspid Aortic Valve: How Does It Function? Why Does It Fail? 2003 STS Presentation, [Abstract Only].
Supplemental European Search Report of EP Application No. 02746781, dated May 13, 2008, 3 total pages.
Supplementary European Search Report issued in European Application No. 05753261.6 dated Jun. 9, 2011, 3 pages total.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3-D Computational Analysis of the Stress Distribution on the Leaflets after Edge to-Edge Repair of Mitral Regurgitation," Journal of Heart Valve Disease, 11:810-822 (2002).
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 14/744,415, Nov. 22, 2017, Office Action.
U.S. Appl. No. 14/744,415, Jun. 1, 2018, Office Action.
U.S. Appl. No. 14/754,274, Mar. 23, 2017, Office Action.
U.S. Appl. No. 14/754,274, May 26, 2017, Office Action.
U.S. Appl. No. 14/754,274, Dec. 4, 2017, Office Action.
U.S. Appl. No. 14/754,274, May 31, 2018, Office Action.
U.S. Appl. No. 14/754,274, Nov. 21, 2018, Notice of Allowance.
U.S. Appl. No. 14/879,726, Oct. 2, 2017, Office Action.
U.S. Appl. No. 14/879,726, Apr. 20, 2018, Office Action.
U.S. Appl. No. 14/879,726, Sep. 5, 2018, Notice of Allowance.
U.S. Appl. No. 14/879,726, Nov. 8, 2018, Notice of Allowance.
U.S. Appl. No. 29/505,404, Jan. 3, 2017, Office Action.
U.S. Appl. No. 29/505,404, Mar. 30, 2017, Office Action.
U.S. Appl. No. 29/505,404, Sep. 26, 2017, Notice of Allowance.
U.S. Appl. No. 16/263,816, filed Jan. 31, 2019, Marsot et al.
U.S. Appl. No. 14/744,415, Jan. 4, 2019, Office Action.

* cited by examiner

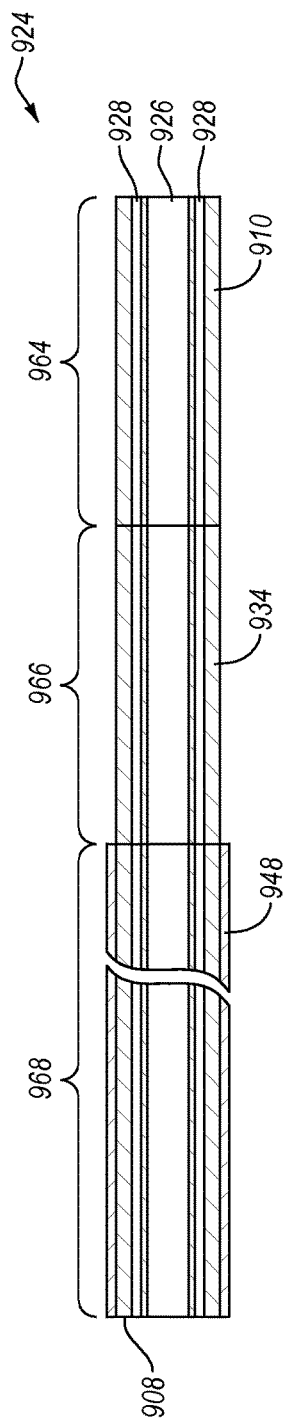
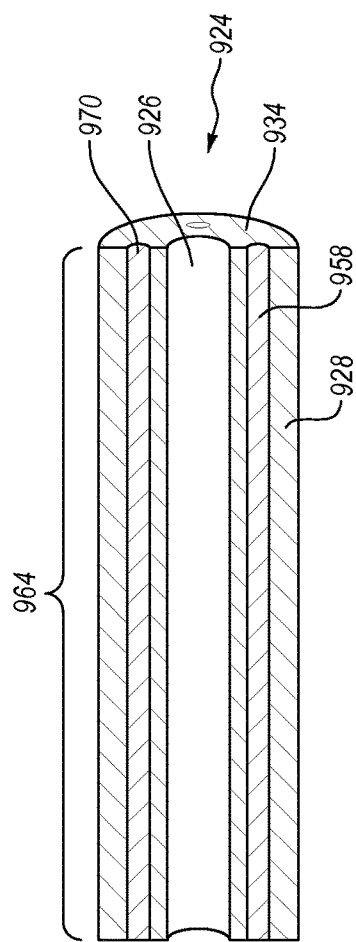
FIG. 10
FIG. 11

DELIVERY CATHETER SYSTEMS, METHODS, AND DEVICES

BACKGROUND OF THE DISCLOSURE

A target location may be accessed from a remote location by passing a catheter system through one or more body lumens to the target location. When the vascular system of the patient is used, the catheter system is inserted into an artery or vein percutaneously or through a small incision in the patient's body to allow the catheter system to be threaded through the patient's body to the target location. When inserting the catheter system percutaneously, an introducer sheath may be used. The introducer sheath creates a pathway or conduit to insert a variety of medical devices into the patient's vasculature and access the target location. For example, the medical devices may include surgical instruments, fiber optic cables, lasers, electronic devices, or sensors capable of monitoring one or more physiological conditions or parameters in the patient's body. Precise delivery of such medical devices may remain a challenge due to the structure at or near the target location, such as in a body cavity or due to the particular demands of the medical device delivered.

Because some medical devices are to be delivered to body cavities, a device advanced into a cavity will protrude into the cavity at approximately the angle in which the device entered the cavity. The catheter system may need to be directed toward the target location within the cavity, if the target location is not in an approximate line with the entry point of the cavity. Additionally, some procedures may require a particular alignment of the medical device beyond a particular placement. The medical device may be steered into position within the cavity after advancing the medical device through the catheter or other delivery system, but for procedures involving the use of multiple medical devices, it may further reduce time and cost of the procedure to steer and align the catheter or other delivery system to provide a consistent delivery of subsequent devices.

For example, to gain access to the left atrium of the heart, the catheter and/or access sheath may be tracked from a puncture in the femoral vein, through the inferior vena cava, into the right atrium and through a puncture in the intra-atrial septum to the left atrium. The pathway can then be used to access the mitral valve, which lies between the left atrium and the left ventricle. Since the mitral valve is located below the point of entry to into the left atrium, devices which are inserted need to be directed downward (i.e., toward the left ventricle) after entry and toward the mitral valve. Additionally, the device used for applying interventional therapies to the mitral valve may necessitate precise alignment with the valve commissures, leaflets, or coaptation line to perform the intended procedure.

The devices can also be directed through the valve chordae or papillary muscles, for example, for interventional therapy to the mitral valve. When such procedures require the use of more than one instrument, each instrument would be dependent upon proper positioning in relation to the valve. Therefore, positioning or steering mechanisms need to be built into each instrument. This adds further cost, complexity, and time to the procedures.

Other procedures may include tracking a catheter and/or access sheath from a puncture in the femoral vein through the intra-atrial septum to the left atrium. This pathway may be used to access the left atrium for ablation of the atrium wall or ablation around the pulmonary veins. Such interventional therapies would require precise alignment with target areas for proper ablation placement. Additionally, alternative access routes and/or access routes to other cavities may be desired.

To overcome some of these challenges, steerable catheter systems include one or more wires that allow manual flexion of the catheter system by an operator at a proximal end of the catheter system. The catheter system may thereby have a distal portion or other portion with an operator-adjustable curvature to allow navigation of the catheter system to the target location. A wire or wires in the catheter system, however, may shift in position within the catheter system. Further, torqueing the catheter system during navigation of the vasculature may cause changes in the position of contents in such catheter systems. Movements of the wires within the guide catheter or delivery catheter may compromise the precision with which the catheter may be oriented in the patient's body or the precision with which the operation and/or deployment of a medical device attached to the distal end thereof may be controlled.

BRIEF SUMMARY OF THE DISCLOSURE

This summary is provided to introduce a selection of concepts that are further described below in the detailed description. This summary is not intended to identify specific features of the claimed subject matter, nor is it intended to be used as an aid in limiting the scope of the claimed subject matter.

In an embodiment, an intravascular device includes an elongated body that defines a major lumen and a plurality of minor lumens. The elongated body has a proximal end and a distal end with a length therebetween. The major lumen and plurality of minor lumens extend through at least a portion of the length of the elongated body. The intravascular device also includes a reinforcement layer connected to the elongated body that includes a reinforcement material that has a greater elastic modulus than a body material of the elongated body.

In another embodiment, an intravascular device includes an elongated body that defines a major lumen and a plurality of minor lumens with a medical device connected to a distal end of the elongated body. The major lumen and plurality of minor lumen extend from a proximal end of the elongated body to the distal end of the elongated body.

In yet another embodiment, a delivery catheter system includes a shaft, a handle, and a control wire. The shaft includes an elongated body that defines a major lumen and a plurality of minor lumen. The elongated body has a proximal end and a distal end with a length therebetween. The handle is operably connected to the proximal end of the elongated body and the control wire is operably connected to the handle. The control wire extends through at least one of the plurality of minor lumens from the proximal end of the elongated body to the distal end of the elongated body.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 10 is a longitudinal cross-sectional view of a delivery catheter, according to at least one embodiment described herein;

FIG. 11 is a longitudinal cross-sectional view of a distal end of a catheter, according to at least one embodiment described herein;

DETAILED DESCRIPTION

Figure 1:
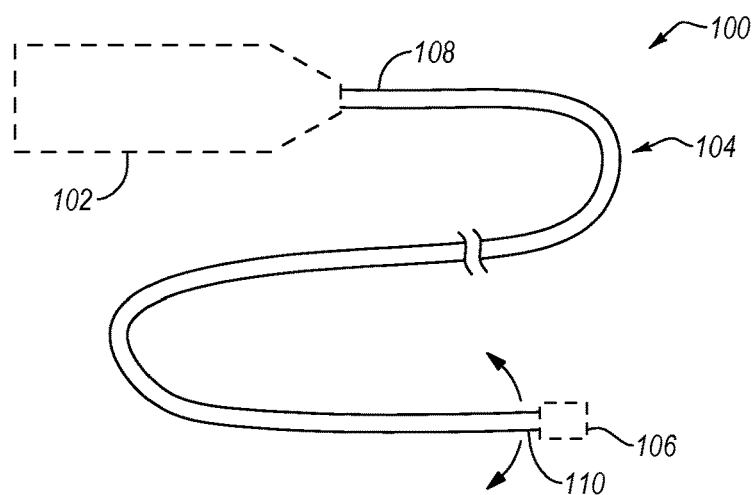
FIG. 1 is a schematic representation of a delivery catheter system, according to at least one embodiment described herein.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using delivery catheter systems or steerable catheters. A delivery catheter system may allow a medical professional to deliver an intravascular or other medical device to a target location in a patient's body. While the present disclosure will describe delivery catheter systems and applications thereof in relation to transvascular procedures in the heart, it should be understood that the devices, systems, and method described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 3 may be combinable an embodiment described in FIG. 9.

A delivery catheter system may have a shaft including a substantially annular body that defines a central, major lumen extending therethrough. The annular body may include a plurality of minor lumen positioned about the major lumen, and providing conduits isolated from the major lumen. The major lumen may include a compression coil therein to promote pushability of the catheter shaft. For example, the compression coil may resist compression and permit lateral flexibility of the shaft. The major lumen may be sized to receive one or more medical devices, including a guidewire, dilation catheters, implantable devices, snares, other medical devices, or combinations thereof.

The minor lumens may be defined by the body of the shaft. For example, the minor lumens may be integrally formed with the body of the shaft. In another example, the minor lumens may be formed by multi-lumen extrusion of one or more materials to form the minor lumens concurrently with the shaft. The minor lumens may, therefore, have defined positions relative to one another and the major lumen, which are fixed relative to the body. The minor lumens may be configured to contain and guide one or more control wires therethrough from a proximal end of the shaft to a distal end of the shaft. In some embodiments, at least one of the wires may be connected to the distal end of the shaft to allow a user to deflect the distal end of the shaft by pushing and/or pulling on the control wire at and/or near the proximal end of the shaft.

FIG. 1 illustrates a schematic representation of a delivery catheter system 100 having a handle 102, a catheter 104, and, optionally, a medical device 106. The handle 102 may be connected to the proximal end 108 of the catheter 104 and may be configured to communicate with one or more lumens of the catheter 104. The medical device 106 may be connected to a distal end 110 of the catheter 104. The one or more lumens of the catheter may allow the handle 102 to communicate with the medical device 106. In at least one embodiment, the medical device 106 may be a replacement heart valve, such as a mitral valve clip that is configured to engage with the mitral valve of a patient's heart. The mitral valve clip may have a one or more moveable elements. In some embodiments, at least one of the lumens of the catheter 104 may allow the handle 102 to deflect the distal end 110 of the catheter. In other embodiments, at least one of the lumens of the catheter 104 may allow the handle 102 to move one or more moveable elements of the mitral valve clip.

While the present application may describe the use of a delivery catheter system 100 in relation to a mitral valve and associated repair and/or replacement, it should be understood that the delivery catheter system 100 may be used in other locations and/or procedures. For example, the delivery catheter system 100 may be used to deliver a medical device to a tricuspid valve for repair and/or replacement. While the mitral valve of the heart is the valve permitting blood flow from the left atrium to the left ventricle (and similarly, limiting or preventing flow in the opposing direction), the tricuspid valve is located between the right atrium and the right ventricle and regulates blood flow therebetween. In some embodiments, the delivery catheter system 100 may be configured to deliver a replacement valve or other medical device for repair of the tricuspid valve through the patient's vasculature and to the right atrium. In other applications, the delivery catheter system 100 may be used to deliver a medical device to other locations of the patient's body through the vasculature or other bodily lumens.

Figure 2:
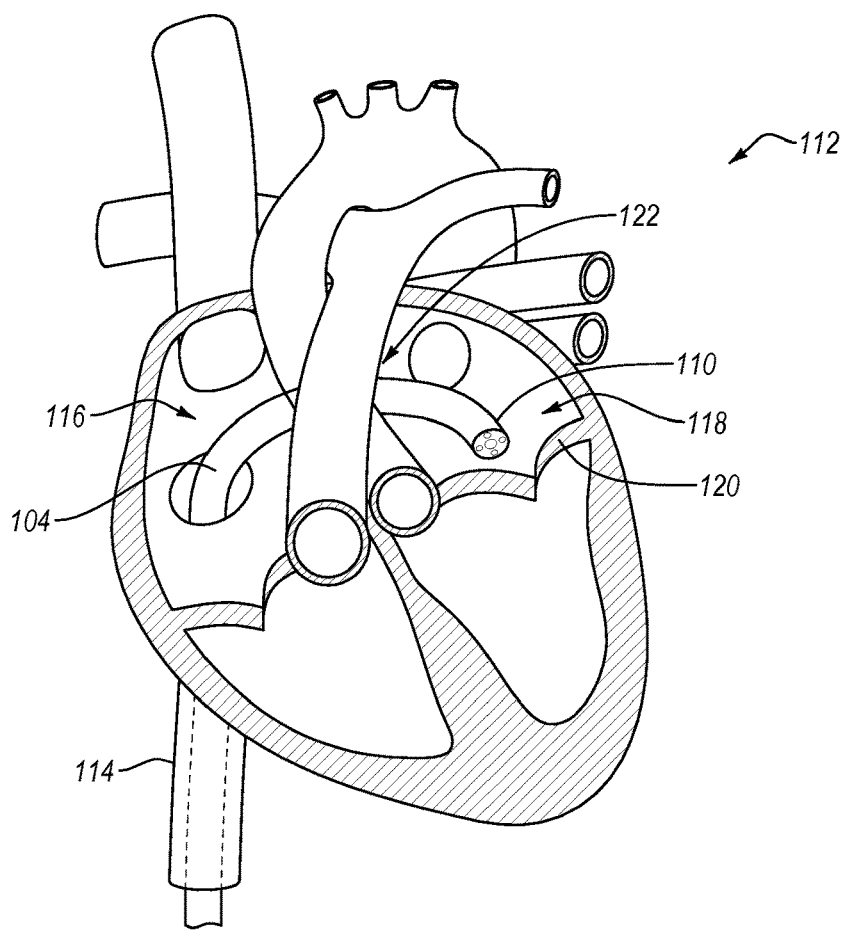
FIG. 2 is a cutaway representation of a delivery catheter that is steerable to the left mitral valve, according to at least one embodiment described herein.

For example, FIG. 2 is a schematic representation of a patient's heart 112 and a medical procedure that may be conducted using a delivery catheter system according to the present disclosure. The catheter 104 (shown in FIG. 2 without a medical device attached thereto) may be inserted into the patient's vasculature and directed to the inferior vena cava 114. The catheter 104 may be urged through the inferior vena cava 114 toward the heart 112 by applying force longitudinally to the catheter 104. Upon entering the heart 112 from the inferior vena cava 114, the catheter 104 enters the right atrium 116. The left atrium 118 must be reached for the catheter 104 to access the mitral valve 120 of the heart 112. The catheter 104 may reach the left atrium 118 through a puncture 122 in the intra-atrial septum. To do so, the distal end 110 of the catheter 104 may be deflected by one or more control wires positioned inside the catheter 104. Precise location of the control wires within the catheter 104 may allow precise control over the deflection of the distal end 110 of the catheter 104. Precise control of the distal end 110 of the catheter 104 may allow for smaller punctures in the intra-atrial septum, more reliable and faster positioning of a mitral clip on the mitral valve, other improvements in the procedures, or combinations thereof. While the present disclosure may provide examples of medical devices 106 and procedures in relation to mitral clip delivery to a patient's heart 112, it should be understood that one of skill in the art may contemplate other applications for a catheter system 100 according to the present disclosure.

Figure 3:
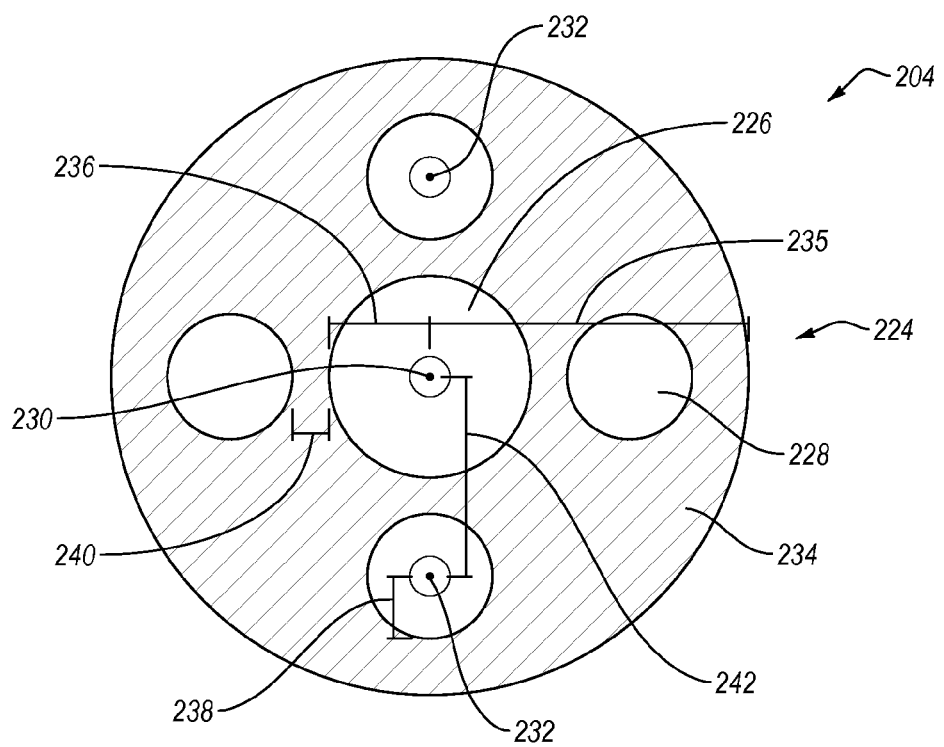
FIG. 3 is a transverse cross-sectional view of a delivery catheter, according to at least one embodiment described herein.

FIG. 3 is a transverse cross-section of an embodiment of a catheter 204 according to the present disclosure. The shaft 224 of the catheter 204 may include a major lumen 226 and one or more minor lumens 228. In some embodiments, the shaft 224 may have a circular transverse cross-section (e.g., the shaft 224 may be substantially cylindrical). In other embodiments, the shaft 224 may have a transverse cross-section that is non-circular, for example, the shaft 224 may have a transverse cross-section that is square, triangular, pentagonal, octagonal, other polygonal, elliptical, regular, irregular, or combinations thereof. The major lumen 226 may be centrally located within the shaft 224 such that the major lumen 226 and shaft 224 share a common longitudinal axis 230. The longitudinal axis 230 is normal to the transverse cross-section depicted in FIG. 3. In other embodiments, the major lumen 226 may be located within the shaft 224 non-coaxially with the longitudinal axis 230 of the shaft 224. For example, the major lumen 226 may be offset within the shaft 224. In another example, the shaft 224 may have a plurality of major lumens 226. The plurality of major lumens 226 may be distributed and/or arranged around the longitudinal axis 230 of the shaft 224.

In some embodiments, the major lumen 226 may be circular in transverse cross-section, while, in other embodiments, the major lumen 226 may have other cross-sectional shapes. In other embodiments, the major lumen 226 may have a transverse cross-section that is square, triangular, pentagonal, octagonal, other polygonal, elliptical, regular, irregular, or combinations thereof. In embodiments with a plurality of major lumen 226, the major lumen 226 may be the same size or may be different sizes. In embodiments with a plurality of major lumen 226, the major lumen 226 may be the same shape or different shapes in transverse cross-section. For example, in a shaft 224 having two major lumens 226 therein, each of the major lumens 226 may have a semi-circular cross-section that complement one another and approximate a circle. In another example, a first major lumen may have a circular cross-section and the second major lumen may have a crescentic cross-section that complimentarily engages and partially surrounds the first major lumen.

The shaft 224 may have a plurality of minor lumens 228. In some embodiments, the minor lumens 228 may be distributed equally about the longitudinal axis 230. For example, the minor lumens 228 may be distributed about the longitudinal axis 230 at equal intervals based upon the quantity of the minor lumens 228. Four minor lumens 228 may be distributed at equal 90° intervals. Three minor lumens 228 may be distributed at equal 120° intervals. In other embodiments, at least two of the minor lumens 228 may substantially oppose one another relative to the longitudinal axis 230 of the shaft 224. Two minor lumens 228 may substantially oppose one another when the minor lumen axes 232 of each of the two minor lumens 228 are symmetrical about a minor plane drawn through the longitudinal axis 230 of the shaft 224. In yet other embodiments, the two minor lumens 228 may substantially oppose one another when the two minor lumens 228 are symmetrical about a mirror plane drawn through the longitudinal axis 230 of the shaft 224 (e.g., the two minor lumens 228 exhibit inversion symmetry about the longitudinal axis 230 of the shaft 224).

The major lumen 226 and minor lumens 228 may be integrally formed with a body 234 of the shaft 224. The body 234 may be made of or include a variety of flexible body materials such as thermoplastic elastomers (TPE). In some embodiments, the body 234 may be a polyether block amide (PEBA). The body 234 may have a constant durometer or may have varying durometer along the longitudinal length of the body 234. For example, the body 234 may be made of or include a body material having a durometer of 35 D to 55 D. In another example, the body 234 may be made of or include a body material that has a durometer of about 45 D. In at least one embodiment, the body material may include PEBAX 4533. In at least another embodiment, the body material may include PEBAX 3533.

The body 234 may be a monolithic extruded body manufactured by a multi-lumen extrusion process. For example, the major lumen 226 and the minor lumens 228 may be formed simultaneously during the extrusion process of the body material to form the body 234 of the shaft 224. In other embodiments, the body 234 may have more than one body material and/or layer of body material. The body 234 may be coextruded and one or more layers may be extruded sequentially or in parallel to build up the body 234 of the shaft 224. For example, an inner portion of the body 234 may be extruded, where the inner portion defines the major lumen 226. An outer portion of the body 234 may be simultaneously or later extruded over the inner portion, where the outer portion defines the minor lumens 228.

The body 234 of the shaft 224 may substantially define the major lumen and the minor lumen relative to one another such that the major lumen 226 and the minor lumen 228 are fixed in position relative to the longitudinal axis 230 of the shaft 224 and fixed in size relative to the size of the body 234. The body 234 of the shaft 224 may have a body radius 235 that is in a range having upper and lower values including any of 0.040 inches, 0.045 inches, 0.050 inches, 0.055 inches, 0.060 inches, 0.065 inches, 0.070 inches, 0.075 inches. 0.080 inches, or any values therebetween. The body radius 235 may be measured from the longitudinal axis 230 of the shaft 224 to an outer surface of the body 234. In embodiments with a non-circular body (e.g., an octagonal body), the body radius 235 may be approximated as the average distance from a longitudinal axis of the non-circular body to an outer surface of the body. In at least one embodiment, the body 234 may have a body radius 235 in a range of 0.050 inches to 0.070 inches. For example, the body radius 235 may be about 0.060 inches.

In some embodiments, the major lumen radius 236 may be within a range of ratios relative to the body radius 235. A major lumen ratio may be the ratio of the major lumen radius 236 to the body radius 235. The major lumen ratio may be within a range having upper and lower values including any of 0.400, 0.425, 0.450, 0.475, 0.500, 0.525, or any value therebetween. For example, the major lumen ratio may be within a range of 0.400 and 0.525. In another example, the major lumen ratio may be within a range of 0.450 and 0.500. In yet another example, the major lumen ratio may be 0.475.

The minor lumen 228 may have a minor lumen radius 238 that is measured from the minor lumen axis 232. A minor lumen ratio may define the minor lumen radius 238 relative to the body radius 235. The minor lumen ratio may be within a range having upper and lower values including any of 0.100, 0.125, 0.150, 0.175, 0.200, or any value therebetween. For example, the major lumen ratio may be within a range of 0.100 and 0.200. In another example, the major lumen ratio may be within a range of 0.125 and 0.175. In yet another example, the major lumen ratio may be 0.150.

As described herein, the body 234 may define the major lumen 226 and the minor lumen 228 and their positions relative to one another. The major lumen 226 and minor lumen 228 may be separated by a portion of the body 234 that defines a lumen wall 240. The lumen wall 240 may be strong enough to prevent puncture and/or rupture of either the major lumen 226 or the minor lumen 228 into the other. For example, the lumen wall 240 may have a thickness relative to the body radius 235. In some embodiments, a wall ratio of the lumen wall 240 thickness relative to the body radius 235 may be within a range having upper and lower values including any of 0.100, 0.110, 0.120, 0.130, 0.140, 0.150, values greater than 0.150, or any value therebetween. For example, the wall ratio may be within a range of 0.100 and 0.150. In another example, the wall ratio may be within a range of 0.110 and 0.140. In yet another example, the wall ratio may be 0.120.

The minor lumen 228 may have a minor lumen axis 232 that is positioned a distance away from the longitudinal axis 230 of the shaft 224. In some embodiments, a minor axis radius 242 may be at least partially dependent on the body radius 235 and may be defined by a minor axis ratio. The minor axis ratio may be within a range having upper and lower values including any of 0.650, 0.675, 0.700, 0.725, 0.750, 0.775, 0.800, 0.825, 0.850, or any value therebetween. For example, the minor axis ratio may be within a range of 0.650 and 0.850. In another example, the minor axis ratio may be within a range of 0.700 and 0.800. In yet another example, the minor axis ratio may be 0.750.

Figure 4:
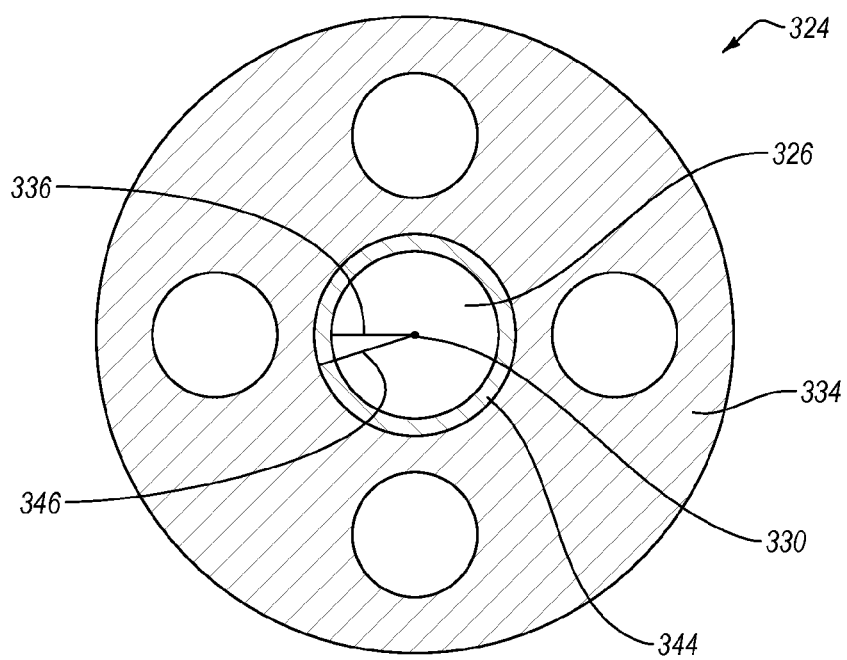
FIG. 4 is a transverse cross-sectional view of another delivery catheter, according to at least one embodiment described herein.

In some embodiments, the shaft 224 may be reinforced (i.e., for increased pushability during use). FIG. 4 depicts another embodiment of a shaft 324 that has a compression coil 344 located within a major lumen 326 of the body 334. The compression coil 344 may be a spiral coil that is made of or includes a resilient coil material. For example, the coil material may be stainless steel, nickel titanium (e.g., Nitinol), other metal alloy, a thermoplastic, other polymer, or combinations thereof. In at least one embodiment, the compression coil 344 may be a stainless steel coil that has a droop value of 11:1 or higher. The compression coil 344 may be sized relative to the major lumen 326 such that the compression coil 344 has an outer diameter ("OD") that is substantially the same as an inner diameter ("ID") of the major lumen 326. In other embodiments, the compression coil 344 may be sized relative to the major lumen 326 such that the compression coil 344 has an OD that is less than the ID of the major lumen 326. In yet other embodiments, the compression coil 344 may be sized relative to the major lumen 326 such that the compression coil 344 has an OD that is less than the ID of the major lumen 326.

When the compression coil 344 has a greater OD than the ID of the major lumen 326, the compression coil 344 may apply a force radially outward on the body 334. When the compression coil 344 has a lesser OD than the ID of the major lumen 326, the body 334 may be less restricted in lateral flexibility by the compression coil 344. In some embodiments, the compression coil 344 may have a coil ratio (i.e., a coil radius 346 to a relaxed major lumen radius 336 measured from a longitudinal axis 320 without the compression coil 344 positioned therein) in a range having upper and lower values including any of 0.80, 0.85, 0.90, 0.95, 1.00, 1.05, 1.10, 1.15, 1.20, or any value therebetween. For example, coil ratio may be within a range of 0.80 and 1.20. In another example, the coil ratio may be within a range of 0.80 and 0.100. In yet another example, the coil ratio may be within a range of 1.00 and 0.120.

The compression coil 344 may provide additional pushability during navigation of a delivery catheter system according to the present disclosure through a lumen of the patient's vasculature or other system. A compression coil 344 that is sized to apply a radial force to the body 334 of the shaft 324 may limit or substantially prevent the movement of the compression coil 344 relative to the body 334, translating forces applied to a proximal end of the catheter to a distal end of the catheter more efficiently than a shaft 324 without a compression coil 344. For example, the compression coil 344 may translate longitudinal force applied to the proximal end of the catheter to a distal end of the catheter more efficiently. In another example, the compression coil 344 may translate torque applied to the proximal end of the catheter to a distal end of the catheter more efficiently.

Figure 5:
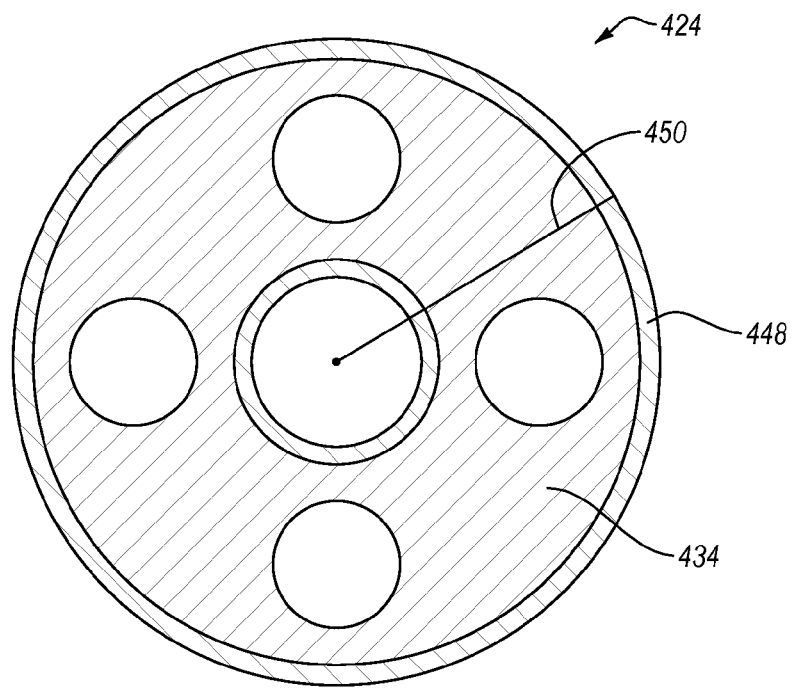
FIG. 5 is a transverse cross-sectional view of a delivery catheter with an outer lining, according to at least one embodiment described herein.

In some embodiments, at least a portion of a shaft may have an outer jacket. FIG. 5 depicts an embodiment of a shaft 424 with an outer jacket 448 affixed thereto. The outer jacket 448 may be made of or include a single material or may be made of or include different materials to impart different handling characteristics on the shaft 424. For example, the outer jacket 448 may be made of or include softer materials to promote flexibility of the shaft 424. In other examples, the outer jacket 448 may be made of or include stiffer materials to promote pushability and/or torqueability of the shaft 424. In yet other examples, the outer jacket 448 may be made of or include lubricious materials to reduce friction between the shaft 424 and the body lumen of the patient. The outer jacket 448 may include PEBA, polytertraflouroethylene ("PTFE"), polyetheretherketone ("PEEK"), other polymers, stainless steel, nitinol, other metals, or combinations thereof. In at least one embodiment, the outer jacket 448 may include a plurality of PEBA materials having different durometers.

In some embodiments, the outer jacket 448 may include a radiopaque marker to improve visualization of the shaft 424 during a medical procedure. For example, the outer jacket 448 may include a barium sulfate (BaSO$_4$), gold, iodine, other radiopaque materials, or combinations thereof in a distal portion of the outer jacket 448. In at least one embodiment, the radiopaque marker may be longitudinally located in a distal and/or intermediate portion of the shaft 424.

Figure 6:
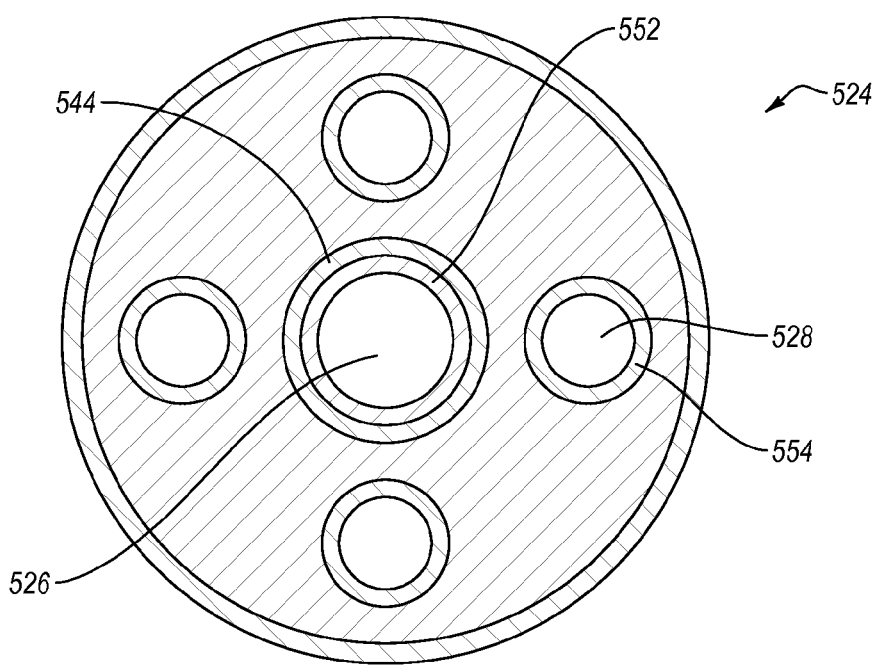
FIG. 6 is a transverse cross-sectional view of a delivery catheter with a minor lumen lining, according to at least one embodiment described herein.

FIG. 6 is a transverse cross-sectional view of a shaft 524 having a lining on a major lumen 526 and minor lumen 528. The major lumen 526 may have a major lumen lining 552 along the surface thereof to provide additional protection for a body 534 of the shaft 524. The major lumen lining 552 may be PTFE, PEEK, other lubricious polymer coating, or combinations thereof. In some embodiments, the major lumen lining 552 may line an inner surface of a compression coil 544, as shown in FIG. 6; while in other embodiments, the major lumen lining 552 may be in direct contact with the body 534. The major lumen lining 552 may provide a substantially continuous surface of the major lumen 526 from a proximal end of the shaft 524 to a distal end of the shaft 524. In other embodiments, the major lumen lining 552 may be located longitudinally within the shaft 524 in a portion less than the entire length of the shaft 524. For example, the major lumen lining 552 may be located in a distal portion of the shaft 524, an intermediate portion of the shaft 524, a proximal portion of the shaft 524, or combinations thereof. The major lumen lining 552 may be distributed continuously within the major lumen 526, or the major lumen lining 552 may be distributed discontinuously (i.e., in a plurality of segments) within the major lumen 526.

Similarly, the minor lumen 528 may have a minor lumen lining 554 along the surface thereof to provide additional protection for a body 534 of the shaft 524. The minor lumen lining 554 may be PTFE, PEEK, other lubricious polymer coating, or combinations thereof. In some embodiments, the minor lumen lining 554 may provide a substantially continuous surface of the minor lumen 528 from a proximal end of the shaft 524 to a distal end of the shaft 524. In other embodiments, the minor lumen lining 554 may be located longitudinally within the shaft 524 in a portion less than the entire length of the shaft 524. For example, the minor lumen lining 554 may be located in a distal portion of the shaft 524, an intermediate portion of the shaft 524, a proximal portion of the shaft 524, or combinations thereof. The minor lumen lining 554 may be distributed continuously within the minor lumen 528, or the minor lumen lining 554 may be distributed discontinuously (i.e., in a plurality of segments) within the major lumen 526. The minor lumen lining 554 may be distributed substantially identically and/or symmetrically among the plurality of minor lumens 528 (e.g., each minor lumen 528 may have the same longitudinal portion lined), or the minor lumen lining 554 may be distributed differently between the plurality of minor lumens 528. For example, a shaft 524 may have four minor lumens 528 as shown in FIG. 6, with two pairs of minor lumens 528 substantially opposing one another one either side of the major lumen 526. In some embodiments, each pair of minor lumen 528 that substantially oppose one another may have minor lumen lining 554 that is distributed substantially the same.

Figure 7:
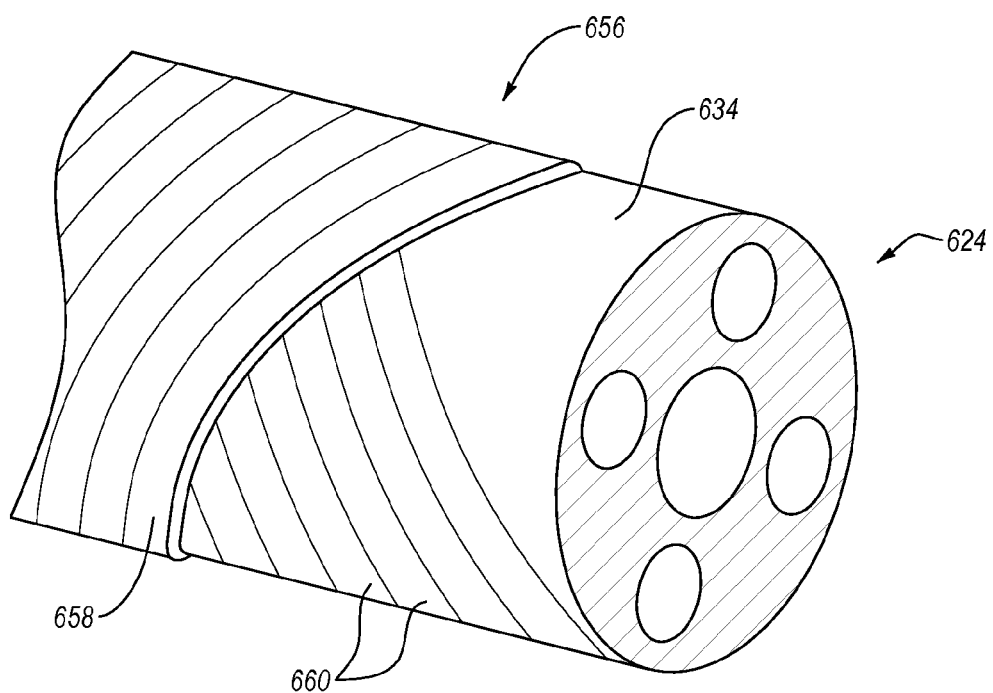
FIG. 7 is a perspective cutaway view of a delivery catheter with layered sheath, according to at least one embodiment described herein.

A reinforcement layer may provide additional structural support and/or additional force transmission ability to the shaft. For example, FIG. 7 depicts a cutaway view of an embodiment of a reinforcement layer 656 layered over a body 634 of a shaft 624. The reinforcement layer 656 may extend circumferentially about the body 634 and may include one or more layers of material. In the depicted embodiment, the reinforcement layer 656 includes two layers 658 of material containing threads 660 that extend helically about the body 634. In other embodiments, the reinforcement layer 656 may contain threads 660 that extend about the body 634 perpendicularly to the longitudinal axis of the shaft 624. In yet other embodiments, the reinforcement layer 656 may contain threads 660 that extend about the body 634 parallel to the longitudinal axis of the shaft 624.

In some embodiments, the reinforcement layer 656 may include a plurality of threads 660 that are woven together to provide one or more layers 658. For example, a layer 658 may include a plurality of threads 660 that extend at an angle to one another and are woven together in a repeating pattern. The plurality of threads 660 may be woven in a diamond two wire two-under-two, over-two pattern; a half-load single wire over-one, one-under pattern; a full-load single wire over-two, under-two pattern; other alternating woven patterns; or combinations thereof. In other embodiments, reinforcement layer 656 may include a single thread 660 routed substantially straight longitudinally through the plurality of threads 660.

The threads 660 may be round threads, elliptical threads, or flat threads. The threads 660 may be made of or include a variety of reinforcement materials, such as, metals, metal alloys, thermoplastics, other polymers, or combinations thereof. In some embodiments, the reinforcement material or materials may have a greater elastic modulus than the body material. For example, the reinforcement layer 656 may include a mixture of threads 660 with different properties, such as stainless steel threads woven with polymer threads. In at least one embodiment, the reinforcement layer 656 may include a plurality of 304 stainless steel wires woven in a diamond pattern. Such an embodiment of the reinforcement layer 656 may include between 16 and 32 threads 660 of stainless steel.

In various embodiments, the reinforcement layer 656 may reinforce different portions of the shaft 624. For example, the reinforcement layer 656 may extend circumferentially about the body 634 to reinforce a longitudinal section of the shaft 624 in a proximal portion of the shaft 624, an intermediate portion of the shaft 624, a distal portion of the shaft 624, or combinations thereof. The reinforcement layer 656 may, thereby, provide torsional, lateral, or longitudinal strengthening of the shaft 624 in different locations to improve navigation of the delivery catheter system through a patient's vasculature or other body lumens.

Figure 8:
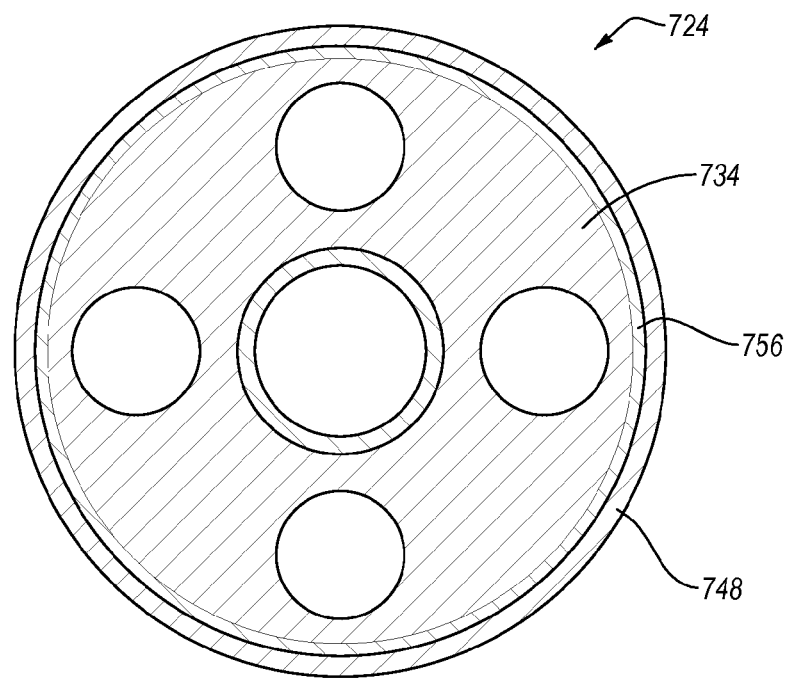
FIG. 8 is a transverse cross-sectional view of a delivery catheter with a layered sheath in the shaft, according to at least one embodiment described herein.

FIG. 8 is a transverse cross-sectional view of another embodiment of a shaft 724. The shaft 724 may include an outer jacket 748, which may be similar to the outer jacket 448 described in relation to FIG. 5, positioned outside of and circumferential around a reinforcement layer 756, which may be similar to the reinforcement layer 656 described in relation to FIG. 7. The outer jacket 748 may encapsulate and/or cover the reinforcement layer 756. The outer jacket 748 may be deposited, extruded, molded, heat shrunk, or otherwise applied to the shaft 724 over the reinforcement layer 756, thereby bonding to the reinforcement layer 756. In some embodiments, at least part of the material of the outer jacket 748 may impregnate a weave of the reinforcement layer 756. Impregnation of the reinforcement layer 756 by at least some of the material of the outer jacket 748 may limit or substantially prevent delamination of the outer jacket 748 from the reinforcement layer 756 and/or body 734.

Figure 9:
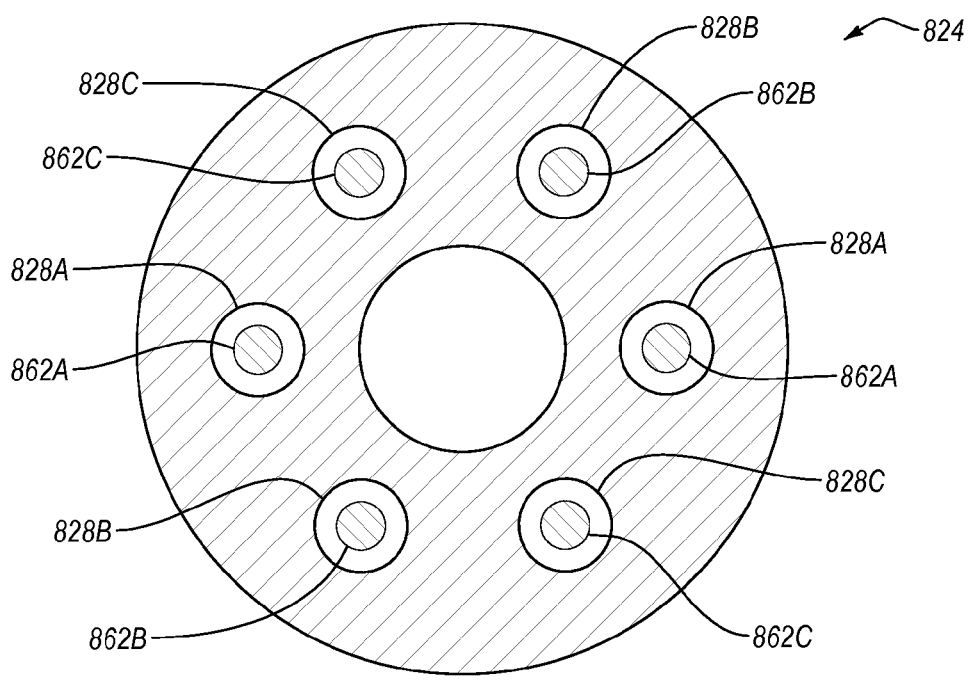
FIG. 9 is a transverse cross-sectional view of a delivery catheter having more than four minor lumens, according to at least one embodiment described herein.

Referring now to FIG. 9, a shaft 824 may have a plurality of minor lumens 828A, 828B, 828C positioned substantially opposing one another. In the depicted embodiment, the shaft 824 has three pairs of minor lumens 828 distributed radially about a major lumen 826. Each pair of minor lumens 828A, 828B, 828C may contain a pair of control wires 858A, 858B, 858C. The control wires 858A, 858B, 858C may extend from a proximal end to a distal end of the shaft 824. The control wires 858A, 858B, 858C may allow a handle (such as that described in relation to FIG. 1) to apply a force to the distal end of the shaft 824 or to a medical device connected to the distal end of the shaft 824. In some embodiments, each pair of minor lumens 828A, 828B, 828C may include a pair of control wires 858A, 858B, 858C. In other embodiments, at least one pair of minor lumens 828A, 828B, 828C may not include a pair of control wires 858A, 858B, 858C. In yet other embodiments, only one minor lumen of a pair may include a control wire.

FIG. 10 is a longitudinal cross-section of a shaft 924 having a proximal portion 960, an intermediate portion 962, and a distal portion 964. The shaft 924 extends from a proximal end 908 to a distal end 910. A body 934 of the shaft 924 may extend from the proximal end 908 to the distal end 910 and may have an outer jacket 948 that extends over at least part of the body 934. For example, the outer jacket 948 depicted in FIG. 10 extends over the proximal portion 960 of the body 934, and the intermediate portion 962 and the distal portion 964 may lack an outer jacket. In other embodiments, the outer jacket 948 may extend over the intermediate portion 962 and/or the distal portion 964. In yet other embodiments, the outer jacket 948 may extend over only a section of the proximal portion 960, the intermediate portion 962, the distal portion 964, or combinations thereof.

The minor lumens 928 may provide conduits through the shaft 924 for control wires that may connect to a medical device connected to the distal end 910 of the catheter. The control wires may allow a handle at the proximal end of the catheter to control the operation and/or deployment of the medical device, such as a mitral valve clip. For example, the control wires may connect to a mitral valve clip to allow control over the opening and/or closing of the clip. The degree to which the clip opens and closes may be controlled by relatively small movements of a control wire. Therefore, the predictable and stable minor lumens may provide increase precision in the placement of a mitral clip.

The shaft 924 may have any length appropriate to access the desired portion of the patient's body. In some embodiments, the shaft 924 may be 60 inches in length. In other embodiments, the shaft 924 may be longer or shorter than 60 inches in length. The proximal portion 960 may form the majority of the shaft 924 and, in some embodiments, a proximal portion ratio of the length of the proximal portion 960 to the length of the shaft 924 may be in a range having upper and lower values including any of 0.70, 0.72, 0.74, 0.76, 0.78, 0.80, 0.82, 0.84, 0.86, 0.88, 0.90, 0.92, 0.94, or any value therebetween. For example, a proximal portion ratio may be in a range of 0.70 and 0.94. In another example, the proximal portion ratio may be in a range of 0.80 to 0.90. In yet another example, the proximal portion ratio may be 0.86. A distal portion ratio of the length of the distal portion 964 to the length of the shaft 924 may be in a range having upper and lower values including any of 0.04, 0.06, 0.08, 0.10, 0.12, 0.14, 0.16, 0.18, 0.20, or any value therebetween. For example, a distal portion ratio may be in a range of 0.04 and 0.20. In another example, the distal portion ratio may be in a range of 0.08 to 0.16. In yet another example, the distal portion ratio may be 0.10. The intermediate portion 962 may account for the remainder in the length of the shaft 924. In some embodiments, the shaft 924 may not include an intermediate portion 962. An intermediate portion ratio of the length of the intermediate portion 962 to the length of the shaft 924 may be in a range having upper and lower values including any of 0.00, 0.02, 0.04, 0.06, 0.08, 0.10, 0.12, 0.14, 0.16, 0.18, 0.20, or any value therebetween. For example, a distal portion ratio may be in a range of 0.00 and 0.20. In another example, the distal portion ratio may be in a range of 0.02 to 0.10. In yet another example, the distal portion ratio may be 0.04.

In at least one embodiment, the shaft 924 includes PEBAX 3533 in the distal portion 964 and PEBAX 4533 in the intermediate portion 962 and proximal portion 960. The body 934 may have a substantially constant outer diameter along the length of the shaft 924. Therefore, the body 934 may have different handling characteristics along the length thereof while maintaining a constant outer diameter. In other embodiments, the distal portion 964 and/or the intermediate portion 962 may include a taper toward the distal end 910. The tapered distal portion 964 may reduce overall material in the body 934 and/or shaft 924 at a given longitudinal position, increasing flexibility of the body 934 and/or tuning a flex profile of the shaft 924.

Figure 12:
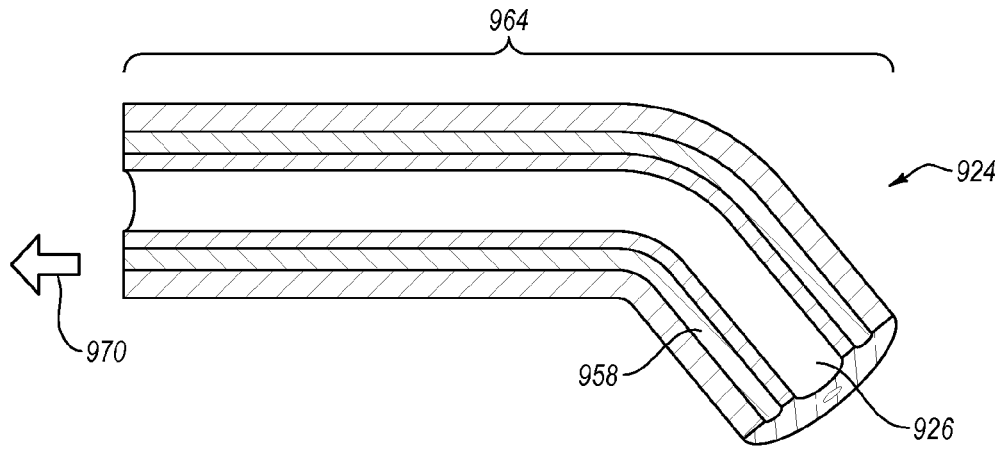
FIG. 12 is a longitudinal cross-sectional view of the distal end of the catheter of FIG. 11 deflected in a first direction, according to at least one embodiment described herein.
Figure 13:
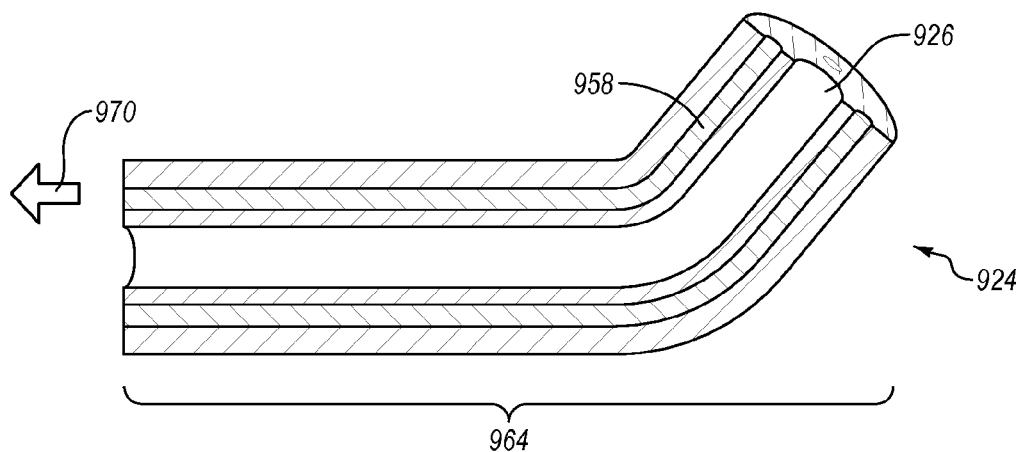
FIG. 13 is a longitudinal cross-sectional view of the distal end of the catheter of FIG. 11 deflected in a second direction, according to at least one embodiment described herein.

FIGS. 11 through 13 depict an embodiment of a catheter that may use the control wires to control the position and/or deflection of the shaft 924, for example, in a steerable catheter application. FIG. 11 depicts the distal portion 964 of the shaft 924 in FIG. 10 with a pair of control wires 958 located in the minor lumens 928. The control wires 958 may connect to the shaft 924 at or near the distal end 910 and extend proximally through the minor lumens. In other embodiments, the control wires 958 may connect to the distal portion 964 of the body 934 not at the distal end 910. As described herein, the control wires 958 may convey forces applied at a proximal end (not shown) of the control wires 958 to the distal end 966 of the control wires 958. The distal end 966 of the control wires 958 may then convey the force to the distal portion 964 of the shaft 924.

FIG. 12 depicts a proximal force 968 applied to a first control wire 958 that is connected to the distal end 910 of the shaft 924. The proximal force 968 may move the first control wire 958 proximally. The movement of the first control wire 958 may then apply a torque to the distal end 910 and rotate and/or deflect the distal end 910 in the transverse direction of the first control wire 958 relative to the major lumen 926. The distal portion 964 of the shaft 924, including the major lumen 926 may then move laterally, providing an arcuate delivery path through the major lumen 926. The major lumen 926 may be positioned using the movement of the control wires 958 to precisely deliver medical devices (such as medical device 106 described in relation to FIG. 1) or other devices or objects within a cavity in the patient's body.

As depicted in FIG. 13, the distal portion 964 of the shaft 924 may be deflected in another direction by the application of a proximal force 968 on a second control wire 958 or on the same first control wire 958 after a 180° rotation of the shaft 924. The shaft 924 may be rotationally symmetrical, as described herein, such that a pair of control wires 958 may produce equal deflection in opposite directions.

Figure 14:
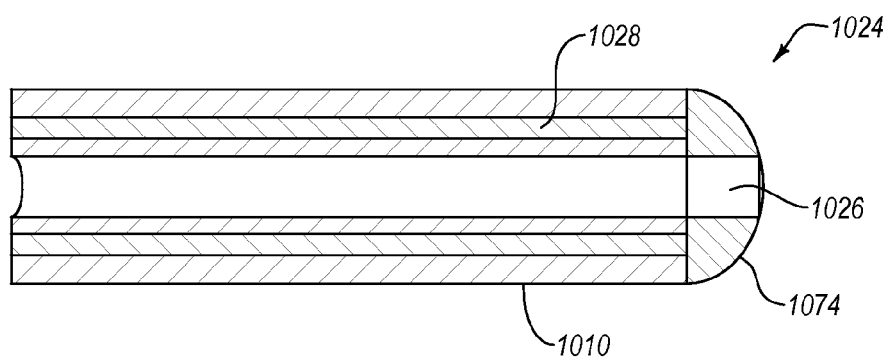
FIG. 14 is a longitudinal cross-sectional view of the distal end of the catheter of FIG. 11 having an atraumatic cap thereon, according to at least one embodiment described herein.

While the catheter shaft has been described herein as delivering a medical device that is connected to a distal end of the shaft, a catheter according to the present disclosure may be configured to navigate a lumen of a patient's body without a device connected thereto and may provide a conduit to guide other devices or equipment to a desired location in the patient's body. For example, FIG. 14 illustrates a side cross-sectional view of a shaft 1024 having an atraumatic tip 1074 located at a distal end 1010. A major lumen 1026 of the shaft 1024 may extend through the atraumatic tip at the distal end 1010 to provide a conduit from a proximal end (not shown) of the shaft 1024.

A catheter system with a shaft having a plurality of lumens defined by the body and fixed in position relative to one another may allow for more precise steering and placement of the catheter system in a patient's body. A medical profession may guide the distal portion of the catheter system to a desired location in a cavity without concern for lumens or other elements within the catheter system shifting relative to one another. Further, in at least some embodiments, a monolithic body defining the plurality of lumens may transmit forces from a proximal end of the shaft to the distal end of the shaft more efficiently and with a lower propensity for kinking or folding of the shaft.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. An intravascular device for delivering a device to a target location within a patient's anatomy, the intravascular device comprising:
   a monolithic elongated body having a proximal end and a distal end, at least part of the elongated body being made of a body material and having a length therebetween;
   a major lumen defined by the elongated body and extending from the proximal end to the distal end;
   a plurality of minor lumen defined by the elongated body and extending from the proximal end through at least a portion of the length of the elongated body, the minor lumen being fixed relative to the major lumen in transverse cross-section, a wall ratio of a thickness of a lumen wall between the major lumen and one of the plurality of minor lumens relative to a radius of the elongated body being within a range of 0.100 and 0.150; and
   a reinforcement layer connected to the elongated body and forming an outer surface of the intravascular device when the intravascular device is used to deliver the device to the target location within the patient's anatomy, the reinforcement layer including a reinforcement material having a greater elastic modulus than the body material.

2. The intravascular device of claim 1, further comprising a radiopaque material in a distal portion of the elongated body.

3. The intravascular device of claim 1, wherein the elongated body has a uniform outer diameter along the length from the proximal end to the distal end.

4. The intravascular device of claim 1, further comprising a compression coil located in the major lumen.

5. The intravascular device of claim 4, wherein the compression coil extends from the proximal end to the distal end.

6. The intravascular device of claim 1, wherein at least two of the plurality of minor lumen are positioned substantially opposite one another relative to the major lumen.

7. An intravascular system device, the intravascular system device comprising:
   an intravascular device configured to deliver a medical device to a target location within a patient's anatomy, the intravascular device comprising:

a monolithic elongated body having a proximal end and a distal end, at least part of the elongated body being made of a body material and having a length therebetween;

a major lumen defined by the elongated body and extending from the proximal end to the distal end, a compression coil being disposed within the major lumen with a lining lining an inner surface of the compression coil to provide substantially continuous surface;

a plurality of minor lumen defined by the elongated body and extending from the proximal end to the distal end of the elongated body, the minor lumen being fixed relative to the major lumen in transverse cross-section, a wall ratio of a thickness of a lumen wall between the major lumen and one of the plurality of minor lumens relative to a radius of the elongated body being within a range of 0.100 and 0.150;

a reinforcement layer connected to the elongated body the reinforcement layer including a reinforcement material having a greater elastic modulus than the body material, the reinforcement layer comprising a first layer of threads layered on a second layer of threads, the first layer of threads comprising a plurality of first threads woven together to form the first layer of threads, a second thread is woven through the first layer of threads in a longitudinal direction along a length of the elongated body; and the medical device releasably connected to the distal end of the elongated body.

8. The device of claim 7, wherein the medical device is a replacement heart valve.

9. The device of claim 7, further comprising a control wire, the control wire extending through one of the plurality of minor lumen and being operably connected to the medical device.

10. The device of claim 9, wherein applying a longitudinal force upon the control wire imparts a force to the medical device, causing a portion of the medical device to move relative to the distal end of the elongated body.

11. A delivery catheter system for delivering a medical device to a target location within a patient's anatomy, the system comprising:

a shaft including:

a monolithic elongated body having a proximal end and a distal end, at least part of the elongated body being made of a body material and having a length therebetween, a major lumen defined by the elongated body and extending from the proximal end to the distal end, a compression coil being disposed within the major lumen with a lining lining an inner surface of the compression coil, a plurality of minor lumen defined by the elongated body and extending from the proximal end through at least a portion of the length of the elongated body, the minor lumen being fixed relative to the major lumen in transverse cross-section, a location of an axis of the minor lumen relative to an axis of the major lumen being defined by a minor axis ratio based upon a radius of the elongated body, the ratio having a value of between about 0.650 and about 0.850, a wall ratio of a thickness of a lumen wall between the major lumen and one of the plurality of minor lumens relative to the radius of the elongated body being within a range of 0.100 and 0.150, and a reinforcement layer connected to the elongated body the reinforcement layer including a reinforcement material having a greater elastic modulus than the body material, the reinforcement layer comprising a first layer layered on a second layer, the first layer remaining closer to the elongated body than the second layer along the length of the elongated body, the first layer comprising a first thread extending circumferentially in a first direction and the second layer comprising a second thread extending circumferentially in a second direction transverse to the first direction;

a handle operably connected to the proximal end of the elongated body; and a control wire connected to the handle extending through at least one of the plurality of minor lumen from the proximal end of the elongated body to the distal end of the elongated body.

12. The system of claim 11, further comprising a lining material positioned between at least part of the wire and a surface of the minor lumen through which the wire extends.

13. The system of claim 11, further comprising the medical device is connected to a distal end of the shaft.

14. The system of claim 11, wherein a distal end of the shaft includes a radiopaque marker thereon.

15. The system of claim 11, further comprising an outer jacket located on an outer surface of the elongated body and extending along at least a portion of the length of the elongated body.

16. The system of claim 11, wherein the handle is configured to apply a longitudinal force to the wire.

* * * * *